United States Patent
Suorsa et al.

(10) Patent No.: US 6,733,456 B1
(45) Date of Patent: May 11, 2004

(54) OFF-APERTURE ELECTRICAL CONNECTION FOR ULTRASONIC TRANSDUCER

(75) Inventors: Veijo T. Suorsa, Sunnyvale, CA (US); David A. White, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 503 days.

(21) Appl. No.: 09/613,819

(22) Filed: Jul. 10, 2000

Related U.S. Application Data

(62) Division of application No. 09/127,089, filed on Jul. 31, 1998, now Pat. No. 6,113,546.

(51) Int. Cl.⁷ .................................................. A61B 8/00
(52) U.S. Cl. ........................................................ 600/459
(58) Field of Search .............................. 600/437, 443, 600/449, 459, 460, 461

(56) References Cited

U.S. PATENT DOCUMENTS

| | | | |
|---|---|---|---|
| 4,101,795 A | * 7/1978 | Fukumoto et al. | .......... 310/336 |
| 4,217,684 A | * 8/1980 | Brisken et al. | .............. 257/416 |
| 4,348,283 A | 9/1982 | Ash | |
| 4,672,591 A | 6/1987 | Breimesser et al. | |
| 4,704,774 A | 11/1987 | Fujii et al. | .................. 29/25.35 |
| 4,794,931 A | 1/1989 | Yock | |
| 4,861,332 A | 8/1989 | Parisi | |
| 4,889,128 A | 12/1989 | Millar | |
| 5,354,220 A | 10/1994 | Ganguly et al. | |
| 5,359,760 A | 11/1994 | Basse et al. | ................. 29/25.35 |
| 5,402,791 A | 4/1995 | Saitoh et al. | ........... 128/662.03 |
| 5,423,220 A | 6/1995 | Finsterwald et al. | ........... 73/642 |
| 5,511,550 A | 4/1996 | Finsterwald | ........... 128/662.03 |
| 5,583,293 A | 12/1996 | Flogel | |
| 5,732,706 A | 3/1998 | White et al. | |
| 5,737,963 A | 4/1998 | Eckert et al. | |
| 5,857,974 A | * 1/1999 | Eberle et al. | ............... 29/25.35 |
| 5,920,972 A | 7/1999 | Palczewska et al. | ........ 29/25.35 |

FOREIGN PATENT DOCUMENTS

| | | | |
|---|---|---|---|
| EP | 0 112 562 | 7/1984 | .......... G10K/11/00 |
| FR | 2325266 | 4/1977 | .......... H04R/1/34 |
| JP | 7322393 | 8/1995 | .......... H04R/17/00 |
| JP | 8307995 | 11/1996 | .......... H04R/17/00 |

* cited by examiner

*Primary Examiner*—Marvin M. Lateef
*Assistant Examiner*—Maulin Patel
(74) *Attorney, Agent, or Firm*—Townsend and Townsend and Crew, LLP

(57) ABSTRACT

The present invention provides catheter systems and imaging assemblies using off-aperture electrical connections for ultrasound transducers. In one embodiment, a catheter includes a transducer connection apparatus (10) comprising a washer (12) having a hole (15) therethrough. A transducer element (24) is at least partially disposed within the washer hole. A matching layer (26) is operably attached to the washer and to the transducer element. The washer, transducer element and matching layer provide an electrical connection between the transducer element and the washer. Signals can be sent to and received from the transducer by establishing an electrical connection with the washer.

20 Claims, 5 Drawing Sheets

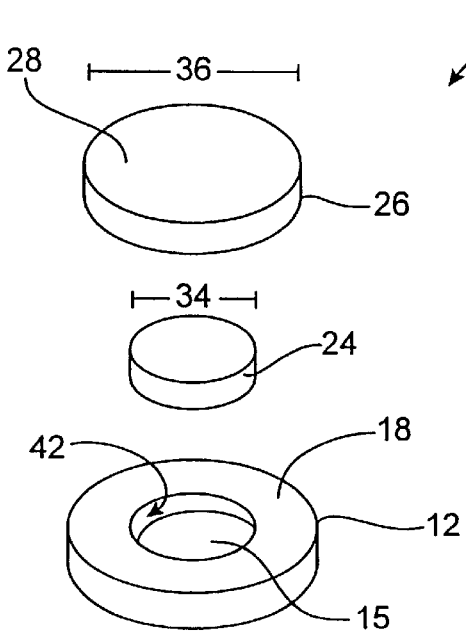
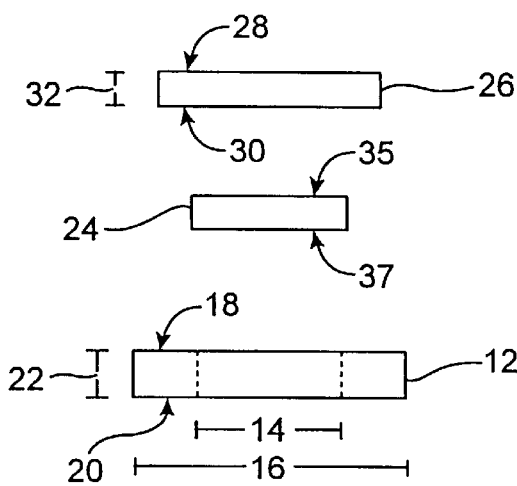
FIG. 1A  FIG. 1B
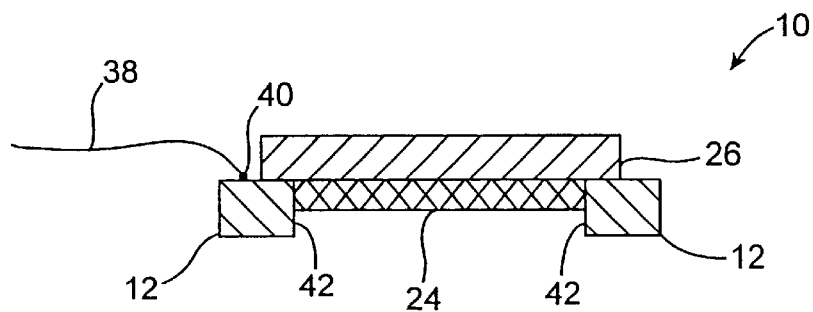
FIG. 1C

OFF-APERTURE ELECTRICAL CONNECTION FOR ULTRASONIC TRANSDUCER

This application is a division of application Ser. No. 09/127,089, filed Jul. 31, 1998, now U.S. Pat. No. 6,113,546.

BACKGROUND OF THE INVENTION

The present invention relates generally to ultrasonic imaging catheters, and more particularly, to catheters having improved electrical connections for ultrasonic transducers.

Intravascular imaging of blood vessels and surrounding tissues continues to be of great benefit in a wide range of medical fields. A particularly successful design for an intravascular imaging catheter employs a rotatable imaging assembly containing an ultrasonic transducer, where the assembly is attached to the distal end of a flexible drive cable. The transducer may be rotated within a catheter body or sheath in order to transmit an ultrasonic signal and produce a video image by well-known techniques. The transducer element or elements are connected to electronics, typically maintained outside the patient's body, to produce the video image.

To connect the transducer to the electronics, an electrode or lead typically is physically attached to either the transducer face, or to the face of a matching layer which is, in turn, attached to the transducer face. However, such an attachment (e.g., a soldered silver attachment point) can adversely affect the transmission and receipt of ultrasonic signals by the transducer. In short, the attachment interferes with or blocks at least part of the transmitted and/or reflected signals. This problem is further exacerbated by the fact that such attachments often are made by hand. Attachments made by hand typically vary in both size and location from catheter to catheter. As a result, it can be difficult to predict the amount of interference the attachment will produce for a particular imaging catheter.

The placement and attachment of the transducer onto the imaging assembly likewise presents difficulties. For example, it often is desirable to attach the transducer element to the imaging assembly so that the element is positioned at a certain angle, or a desired offset, with respect to the assembly centerline. For transducers that are placed and affixed by hand, the angle and offset can vary between otherwise identical catheters.

SUMMARY OF THE INVENTION

The present invention provides off-aperture electrical connections for ultrasound transducers, imaging assemblies and catheters employing such connections, and methods for their use. The electrical connections of the present invention are intended to overcome at least some of the problems of the prior art. For example, connections of the present invention move the electrode or front lead attachment off-aperture, or off the transducer face. This reduces or eliminates the interference such attachment points may cause to the ultrasound signals transmitted from and/or received by the transducer element. Further, imaging assemblies of the present invention are designed to reduce or eliminate the catheter-to-catheter variations in the transducer's offset and angular position with respect to the assembly housing centerline. Such assemblies are hence more uniform and predictable.

In one embodiment, the present invention provides a transducer connection apparatus. The connection apparatus includes a washer having a hole therethrough and a transducer element that is at least partially disposed within the washer hole. A matching layer is operably attached to the washer and to the transducer element such that an electrical connection is provided between the washer and the transducer element. In this manner, signals can be sent from, and received by, the transducer by establishing an electrical connection with the washer. For example, in one aspect, a lead is operably attached to the washer. Preferably, this lead also is attached to an electrical signal source to send electrical signals to the transducer element for ultrasound imaging. The electrical connection is made with a reduced concern as to the size or precise location of the attachment point because the lead or other electrical connection device is attached to the washer and not to the transducer or matching layer face.

In one aspect, the matching layer includes a material having an acoustic impedance that is lower than an impedance of the transducer element. Such a matching layer is particularly useful since transducer elements typically have a significantly higher impedance than an impedance of the surrounding tissue being imaged.

In another aspect, at least a portion of the matching layer includes an electrically conductive material. In this manner, the matching layer helps facilitate an electrical connection between the transducer element and the washer. In one aspect, the transducer connection apparatus matching layer has first and second matching layer surfaces defining a thickness therebetween. The second matching layer surface is operably attached to the washer and to the transducer element. In one aspect, the second matching layer surface incudes an electrically conductive material. Preferably, the second matching layer surface is operably attached to the washer using an electrically conductive adhesive material. Alternatively, the second matching layer surface is operably attached to the washer using an electrically non-conductive adhesive material, an ultrasonic or thermal bond, or the like.

In one aspect, the washer includes a flexible circuit, such as a polyimide having at least one electrode. The electrode may be a gold-plated electrode pattern, a copper electrode pattern, or the like. Preferably, at least a portion of the washer comprises an electrically conductive material.

In another aspect, the washer has first and second washer surfaces, an outer diameter and an inner diameter. The washer outer diameter preferably is greater than a matching layer diameter. In this manner, the matching layer and washer can be operably attached to one another, while leaving a portion of the washer exposed to permit a lead or electrode to be attached thereto. The washer and matching layer also may have an elliptical or oval shape. In such a case, the washer has an outer major axis and an inner major axis, with the washer outer major axis being greater than a matching layer major axis. In one aspect, the first washer surface comprises an electrically conductive material and is operably attached to the matching layer. In another aspect, a lead is operably attached to the first washer surface.

In one particular aspect, the transducer element has an outer diameter or major axis that is about equal to the washer's inner diameter or inner major axis, respectively. In this manner, the transducer element is disposed within the washer hole so that the transducer element is in communication with an inner edge of the washer. The transducer element may be operably attached to the washer inner edge using an electrically conductive epoxy or the like. Alternatively, the transducer element may have an outer diameter or major axis that is less than the washer inner diameter or inner major axis. This configuration creates a gap between the transducer element and the washer's inner edge when the transducer element is disposed within the washer hole.

In one aspect, the transducer element, washer and matching layer are all generally disk-shaped, although other shapes are possible within the scope of the present invention. Similarly, the matching layer preferably has a diameter or major axis that is greater than the transducer element's diameter or major axis. Such a relationship facilitates electrical connections between the transducer element and matching layer, and between the matching layer and washer. In one aspect, the washer has a thickness that is greater than the transducer element's thickness. In this manner, the transducer element may be completely disposed within the washer hole.

In one particular embodiment, a transducer connection apparatus, ostensibly as previously described, further includes a bond layer operably attached to the transducer element. In one aspect, the bond layer is at least partially disposed within the washer hole. The matching layer is operably attached to the washer and bond layer such that an electrical connection is established between the washer and the transducer element. In this manner, the bond layer acts as a second matching layer for the transducer element. In one particular aspect of the embodiment, the bond layer includes an electrically conductive adhesive material for bonding the transducer element and washer to the matching layer. Alternatively, the bond layer comprises an electrically non-conductive adhesive material for bonding the transducer element and washer to the matching layer. In one aspect, the non-conductive bond layer further includes an electrode operably attached to the transducer element and washer.

The invention further provides an exemplary imaging assembly, which includes a housing having a distal end, a proximal end and a longitudinal axis. A transducer connection apparatus is operably attached to the housing. The connection apparatus includes a washer having a hole therethrough and a transducer element that is at least partially disposed within the washer hole. A matching layer is operably attached to the washer and to the transducer element such that an electrical connection is provided between the transducer element and washer.

In one aspect, the imaging assembly further includes a lead operably attached to the washer. In another aspect, the housing and lead are adapted to be attached to a cable. Preferably, the housing and lead are adapted to be attached to an integrated coaxial/drive cable.

In one particular aspect, a portion of the housing forms a generally flat surface to which the connection apparatus is operably attached. In one aspect, the surface is positioned generally parallel to the housing longitudinal axis. Alternatively, the surface is positioned to form a desired angle with the housing longitudinal axis, preferably, an angle that is between about −60 degrees and about +60 degrees, and more preferably, between about −15 degrees and about +15 degrees.

In one aspect, the housing preferably is formed with a throughhole. The washer is operably attached to the surface to at least partially cover a first opening of the throughhole.

In one aspect, a backing material is provided within the throughhole, preferably, a backing comprising sound-attenuating material. In one aspect, the backing material includes an electrically conductive material, and the transducer element is in electrical communication with the backing. In this manner, a back side electrical connection or negative connection or ground can be formed between the housing and the transducer element. In another aspect, the transducer element is in electrical communication with the housing.

Alternatively, the backing material comprises an electrically non-conductive material. An electrode is provided that is operably attached to the transducer element and the housing. In this manner, the electrode provides a back side electrical connection or negative connection or ground from the transducer element to the housing. In another aspect, the transducer element is fully disposed within the washer hole. In one aspect, the housing includes a cap to enclose a second opening of the throughhole to form an air-filled cavity. In this matter, air operates as the backing material. In another aspect, the assembly further comprises an electrode that is operably attached to the transducer element and to the washer to provide a second electrical connection therebetween.

In one embodiment, an imaging assembly according to the present invention includes a housing having a distal end, a proximal end and a longitudinal axis. The housing is formed with an air-filled cavity. A transducer connection apparatus is operably attached to the housing to at least partially cover an opening of the cavity. The connection apparatus includes a washer having a hole therethrough and a transducer element that is at least partially disposed within the washer hole. A first matching layer is operably attached to the washer and to the transducer element so that an electrical connection is provided between the transducer element and washer.

In one aspect, the transducer element is in electrical communication with the housing. In another aspect, the imaging assembly further includes a second matching layer operably attached between the transducer element and the first matching layer.

The invention further provides an exemplary catheter system which includes a catheter body having a distal end, a proximal end and a working lumen. A cable, preferably an integrated coaxial/drive cable, is disposed within the working lumen and an imaging assembly is operably attached to a distal end of the cable. The imaging assembly includes a housing and a transducer connection apparatus operably attached to the housing. The connection apparatus includes a washer having a hole therethrough, a transducer element that is at least partially disposed within the washer hole, and a matching layer operably attached to the washer. The transducer element is in electrical communication with both the housing and the cable.

The present invention further provides exemplary methods of imaging a body lumen. One such method includes providing a catheter system including a catheter body having a distal end, a proximal end and a working lumen. A drive cable and a transmission line are disposed within the working lumen. A housing as previously described is operably attached to the drive cable. The housing includes a transducer connection apparatus as previously described. The method includes inserting the catheter body into a body lumen, energizing the transducer element, capturing a reflected signal and producing an image of the body lumen based on the reflected signal.

Other features and advantages of the invention will appear from the following description in which the preferred embodiment has been set forth in detail in conjunction with the accompanying drawings.

BRIEF DESCRIPTION OF THE DRAWINGS

FIGS. 1A and 1B provide exploded overall and exploded side views, respectively, of a transducer connection apparatus according to the present invention;

FIG. 1C is a cross-sectional side view of the transducer connection apparatus depicted in FIGS. 1B and 1C;

DESCRIPTION OF THE PREFERRED EMBODIMENT

Figure 2A:
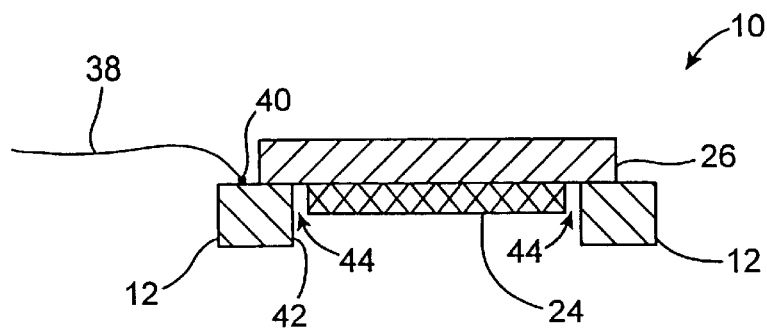
FIGS. 2A–D depict cross-sectional side views of alternative transducer connection apparatus according to the present invention.

FIGS. 1A–1C depict one embodiment of a transducer connection apparatus 10 according to the present invention.

Transducer connection apparatus 10 includes a washer 12. Washer 12 has an outer diameter 16 and an inner diameter 14 defining a washer hole 15. Washer 12 further includes a first washer surface 18, a second washer surface 20 and a washer thickness 22.

Connection apparatus 10 includes a transducer element 24 having a diameter 34, a first face 35 and a second face 37. Transducer element diameter 34 and washer inner diameter 14 are adapted to allow transducer element 24 to be at least partially disposed within washer hole 15. Transducer element 24 may comprise piezocomposite materials, piezoceramics (such as PZT), piezoplastics, and the like.

Connection apparatus 10 further includes a matching layer 26, having a first matching layer surface 28, a second matching layer surface 30, a matching layer thickness 32 and a matching layer diameter 36. Matching layer 26 is operably attached to washer 12, and preferably, is operably attached to first washer surface 18.

Preferably, washer outer diameter 16 is greater than matching layer diameter 36, and matching layer diameter 36 is greater than transducer element diameter 34. Transducer element 24 is disposed within washer hole 15 so that matching layer 26 is operably attached to washer 12 and to transducer element 24, and more preferably to transducer first face 35. Alternatively, matching layer 26 and transducer element 24 are proximate each other to provide for an electrical connection therebetween. In some cases transducer element 24 may be partially disposed within washer hole 15, such as when transducer element 24 has a thickness that is greater than washer thickness 22.

While FIGS. 1A–1C depict washer 12, transducer element 24 and matching layer 26 as generally disk-shaped, these components may have a variety of shapes within the present invention. For example, washer 12, transducer element 24 and matching layer 26 may be generally elliptical or oval in shape. In such a configuration, diameters 34 and 36 would be major axis 34 and 36, outer diameter 16 would be an outer major axis 16 and inner diameter 14 would be an inner major axis 14.

The physical arrangement of washer 12, transducer element 24 and matching layer 26 permit an electrical connection to be established between transducer element 24 and washer 12. Such a connection may be accomplished using a variety of methods. For example, washer 12 and matching layer 26 may at least partially comprise electrically conductive materials. In this manner, electrical signals may be transferred between washer 12 and matching layer 26, and between matching layer 26 and transducer element 24.

More preferably, as shown in FIG. 1C, second matching layer surface 30 is operably attached to both transducer element 24 and washer first surface 18 using a thin layer of electrically conductive or non-conductive adhesive (not shown). The adhesive layer is thin enough to be generally acoustically transparent.

The use of an electrically conductive adhesive layer establishes an electrical connection between transducer element 24 and first washer surface 18. The adhesive layer provides the electrical conductive path between transducer element 24 and washer first surface 18. Further, the use of electrically conductive adhesive permits the use of matching layer 26 comprising either electrically conductive materials, such as silver-filled epoxy, tungsten-filled epoxy, or the like, or electrically non-conductive materials, such as mylar, polyimide, polyurethane or the like.

Alternatively, matching layer 26 can be operably attached to transducer element 24 and first washer surface 18 using a thin layer of electrically non-conductive adhesive. In such an embodiment, matching layer 26 comprises an electrically conductive material, or second matching layer face 30 is coated with an electrically conductive material. The non-conductive adhesive layer is thin enough to permit a molecular contact between transducer first face 35 and second matching layer surface 30. The result is an ohmic, electrically-conductive contact. In addition, some roughness to the second matching layer surface 30, or to transducer first face 35 facilitates an electrically conductive bond. Similarly, second matching layer surface 30 is electrically coupled to first washer face 18.

Washer 12 may comprise electrically conductive materials, such as brass, copper, stainless steel or the like. Washer 12 also may comprise electrically non-conductive materials, such as polyimide, vinyl, mylar or the like. For washer 12 comprising electrically conductive material, a lead 38 may be attached using an attachment point 40 made directly to washer 12. Lead 38 then may be connected to other electronics, such as to ultrasound imaging equipment and the like. For washer 12 comprising electrically non-conductive material, washer 12 may require an electrode, electrically conductive film, or the like to be attached to washer 12 in order to complete an electrical connection to transducer element 24.

Washer 12 also may comprise a flexible circuit board. A flex circuit typically consists of a substrate, for example a polyimide substrate, and an electrode pattern, preferably comprising a gold-plated or a copper electrode pattern. The flex circuit electrodes are electrically connected to lead 38 and to either an electrically conductive adhesive or to matching layer 26 to permit washer 12 to be in electrical communication with transducer element 24.

Once washer 12 and transducer element 24 are in electrical communication, electrical signals may be sent to and received from transducer element 24 by connecting electronics, such as ultrasound imaging equipment, to washer 12.

As best shown in FIG. 1C, transducer element diameter 34 is about equal to washer inner diameter 14, so that transducer element 24 is in contact with an inner edge 42 of washer 12. Transducer element 24 may be operably attached to washer 12 using electrically conductive epoxy, electrically non-conductive epoxy, or the like. Such material also may serve as a transducer backing material, depending upon the method used to establish a back side electrical connection, negative contact or ground for the transducer, as further described below. Physical contact between transducer element 24 and washer inner edge 42 results in transducer element 24 and washer 12 being acoustically coupled. Such a relationship does not significantly degrade transducer element 24 operation, provided that washer 12 comprises material that is acoustically lossive, such as epoxy, rubber or the like.

In order to send electrical signals to, or receive signals from, transducer element 24, an electrical connection only need be made to washer 12. Apparatus 10 thereby eliminates the need to solder or otherwise affix an electrical connection, such as lead 38, directly to transducer element 24 or to matching layer 26. Lead attachment point 40, which may include silver, gold/chrome, gold/chrome/nickel, copper or the like, is made to washer 12. By making attachment point 40 to washer 12, instead of to transducer element first face 35 or to first matching layer surface 28, attachment point 40 does not interfere with ultrasound signals sent and/or received by transducer element 24. As a result, the variability of attachment point 40 size and location is a reduced concern due to its minimal impact on transducer element 24 performance.

Turning now to FIGS. 2A–2D, alternative connection apparatus according to the present invention will be described. FIG. 2A depicts connection apparatus 10 as previously described in conjunction with FIGS. 1A–1C, with the exception that transducer element diameter 34 is smaller than washer inner diameter 14. This results in a gap 44, preferably an air-filled gap, between transducer element 24 and washer inner edge 42. In such an embodiment, transducer element 24 is operably attached to matching layer 26, or to other components of an imaging assembly (not shown in FIG. 2). The back side electrical connection to transducer element 24 is made using electrically conductive transducer backing (see FIG. 3A).

Figure 2B:
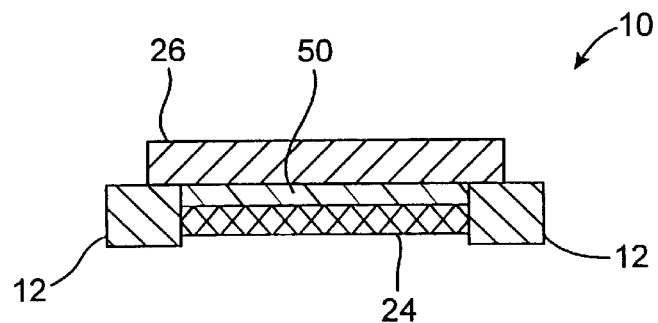
Figure 2C:
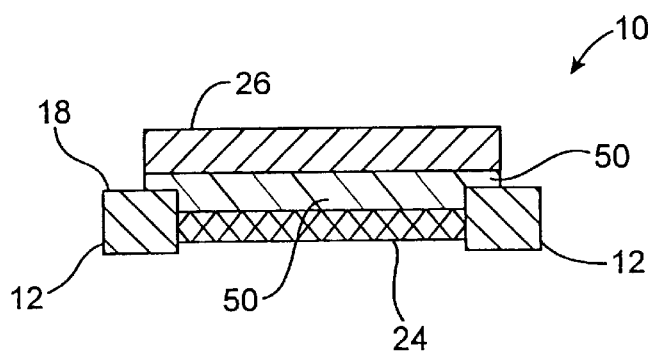

Transducer connection apparatus 10 depicted in FIGS. 2B and 2C are similar to apparatus 10 described in conjunction with FIG. 1, with the exception that the adhesive film is enlarged to comprise a bond layer 50. Bond layer 50 preferably comprises an electrically conductive, adhesive material to operably attach matching layer 26 to washer 12 and transducer element 24. For example, bond layer 50 may comprise silver epoxy or the like. Bond layer 50 further preferably has an ultrasound impedance that is between the impedance of transducer element 24 and the impedance of matching layer 26. Such relative impedances facilities an in-phase alignment of the ultrasonic signal propagated by transducer element 24 with the portion of the propagated signal reflected by bond layer 50. Multiple matching layers result in improved efficiency and band width compared to single matching layer designs due, in part, to providing smaller, but more frequent impedance changes between the transducer and the surrounding tissue or fluid being imaged.

FIG. 2B depicts bond layer 50 fully disposed within washer hole 15. In such a configuration, matching layer 26 preferably is electrically conductive to provide an electrical connection between matching layer 26 and washer 12. As a result, an electrical connection between transducer element 24 and washer 12 is established. Alternatively, second matching layer surface 30 can comprise electrically conductive material, or be coated with electrically conductive material to facilitate an electrical connection between bond layer 50 and washer 12.

FIG. 2C depicts bond layer 50 being partially disposed within washer hole 15. Such an arrangement is particularly useful when matching layer 26 comprises an electrically non-conductive material. Electrically conductive bond layer 50 provides the electrical connection between transducer element 24 and first washer surface 18.

Figure 2D:
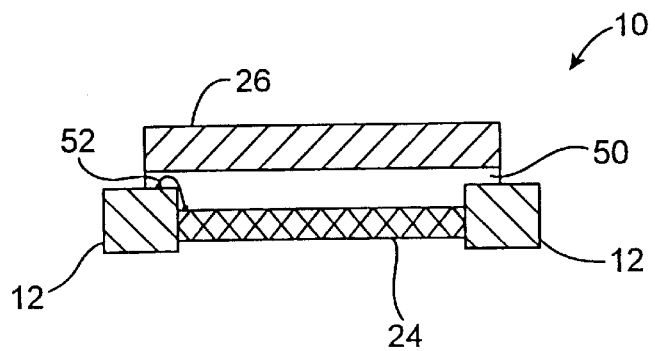

FIG. 2D depicts transducer connection apparatus 10 having bond layer 50 comprising an electrically non-conductive material. Bond layer 50 (not cross-hatched for convenience of illustration) contains an electrode or lead 52, which operably connects transducer element 24 to washer 12. In this manner, lead 52 transmits electrical signals from transducer element 24 to washer 12. Alternatively, bond layer 50 may comprise electrically non-conductive material and be fully disposed within washer hole 15 (as depicted in FIG. 2B). In such an embodiment, matching layer 26 preferably comprises electrically conductive material and lead 52 provides an electrical connection between transducer element 24 and second matching layer surface 30. Second matching layer surface 30 is in electrical communication with washer 12. As will be appreciated by those skilled in the art, modifications may be made to the above described embodiments within the scope of the present invention. For example, additional matching layers may be added, provided the desired electrical connection between transducer element 24 and washer 12 is maintained.

Figure 3A:
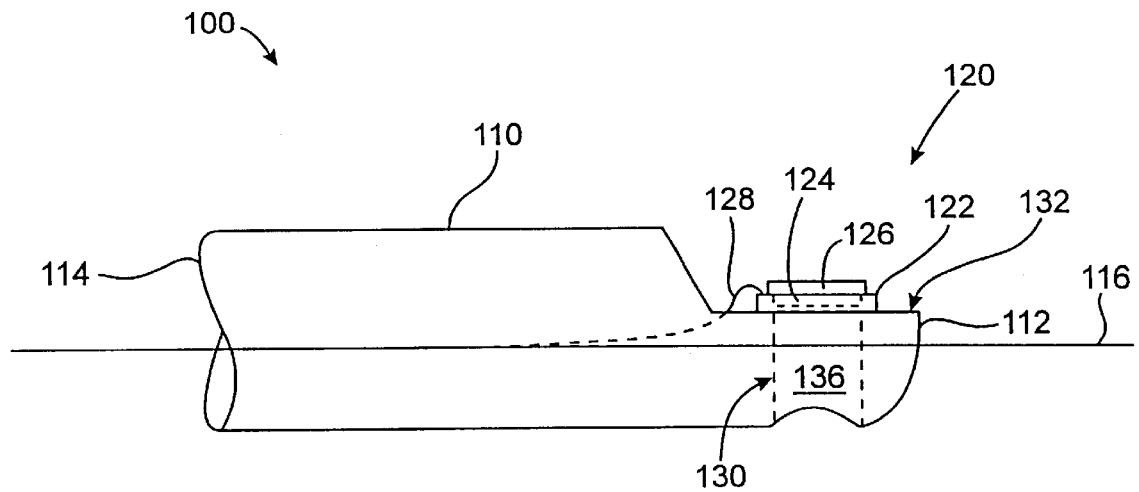
FIGS. 3A and 3B depict side views of alternative imaging assemblies according to the present invention.
Figure 3B:
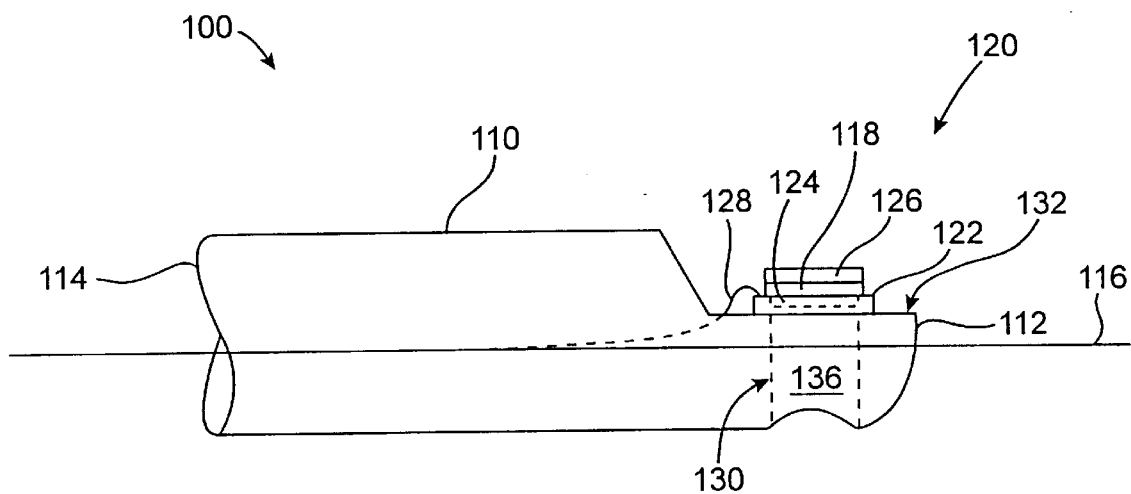

Turning now to FIGS. 3A and 3B, exemplary imaging assemblies according to the present invention will be described. An imaging assembly 100 comprises a housing 110, having a distal end 112, a proximal end 114 and a longitudinal axis 116. While housing 110 is shown to have a generally cylindrical shape, other housing 110 shapes are possible within the scope of the present invention. Housing 110 preferably comprises a hollow housing for embodiments having a throughhole with solid transducer backing, although a solid housing can be used within the scope of the present invention. Housing 110 preferably comprises stainless steel, nickel-plated steel, tin-plated steel, gold-plated steel or the like. Such materials provide sufficient mechanical strength to enable housing 110 to be operably attached to a cable, such as a stainless steel drive cable (not shown in FIG. 3). Housing 110 also can comprise an epoxy-like material, plastics or the like. Such materials provide desirable sound attenuating and/or electrical conductivity properties.

Imaging assembly 100 further includes a transducer connection apparatus 120. As previously described in conjunction with FIGS. 1 and 2, connection apparatus 120 includes a washer 122, a transducer element 124, a matching layer 126 and a lead 128 operably attached to washer 122. FIG. 3A depicts an embodiment without a bond layer. FIG. 3B depicts an embodiment having a bond layer 118 as previously described. Bond layer 118 is between matching layer 126 and transducer element 124, and is operably attached to washer 122 surface. Housing 110 further includes a throughhole 130 formed through at least a portion of housing 110, and a generally flat surface 132 located near distal end 112. Connection apparatus 120 is operably attached to surface 132 in a manner which positions transducer element 124 over an opening to throughhole 130. Washer 122 further operably attaches to surface 132 in a manner which positions transducer element 124 at a known offset from longitudinal axis 116. Offset is defined as the distance the transducer element 124 upper surface is located away from axis 116. Furthermore, transducer element 124 is positioned at a known angular relationship to axis 116 by operably attaching washer 122 to surface 132. FIG. 3 depicts surface 132, transducer 124 and axis 116 as being generally parallel.

For housing 110 comprising stainless steel, or the like, it is preferable to have transducer element 124 fully disposed within the washer hole (as shown in FIG. 3), because lateral coupling to hard materials such as steel is acoustically undesirable. For housing 110 comprising epoxy, plastics or the like, transducer element 124 can extend into throughhole 130 without degrading transducer element 124 performance.

Throughhole 130 preferably is filled with a backing material 136. Backing material 136 is selected to have sound attenuating qualities so that ultrasound signals propagated into the backing are not reflected by backing material 136, which would result in artifacts. Backing material 136 may comprise electrically conductive material, such as epoxy, silver/tungsten epoxy or the like. In such an embodiment, transducer element 124 preferably rests on, and/or is operably attached to, backing material 136. In this manner, electrically conductive backing material 136 provides a back side electrical connection or negative conductive path, or ground, between transducer element 124 and housing 110.

Alternatively, backing material 136 may comprise electrically non-conductive material, such as epoxy, polyurethane, rubber or the like. In such an embodiment having non-conductive backing, transducer element 124 preferably has a second lead (not shown) to connect the throughhole-facing surface of transducer element 124 to housing 110. Other methods of creating an electrical connection between transducer element 124 and housing 110 are possible. For example, electrically conductive epoxy, or the like can be used to directly connect the throughhole-facing surface of transducer element 124 to housing 110. Transducer element 124 also may be grounded by connecting transducer element 124 directly to an electrically conductive washer 122 that is, in turn, connected to housing 110. Such a connection may be made using electrically conductive epoxy or the like. Washer 122 can provide both the positive and negative connection provided that the two are kept separate. For instance, a center conductor and shield of a miniature coaxial cable can be terminated to the washer, which provides both the positive and negative connection to transducer element 124.

Imaging assembly 100 therefore provides a way to move the electrical attachment point for lead 128 to washer 122. Imaging assembly 100 further positions transducer element 124 at a known offset and angular relationship to axis 116 by mounting connection apparatus 120 to surface 132. In contrast, manually positioned and attached transducer elements are typically attached within throughhole 130. Such transducer elements have an offset and angular relationship that can vary between otherwise identical imaging assemblies. Lead 128 preferably is adapted to be in communication with a cable, and more preferably, with an integrated coaxial/drive cable. In this manner, electrical signals can be sent to, and received from, transducer element 124.

Figure 4B:
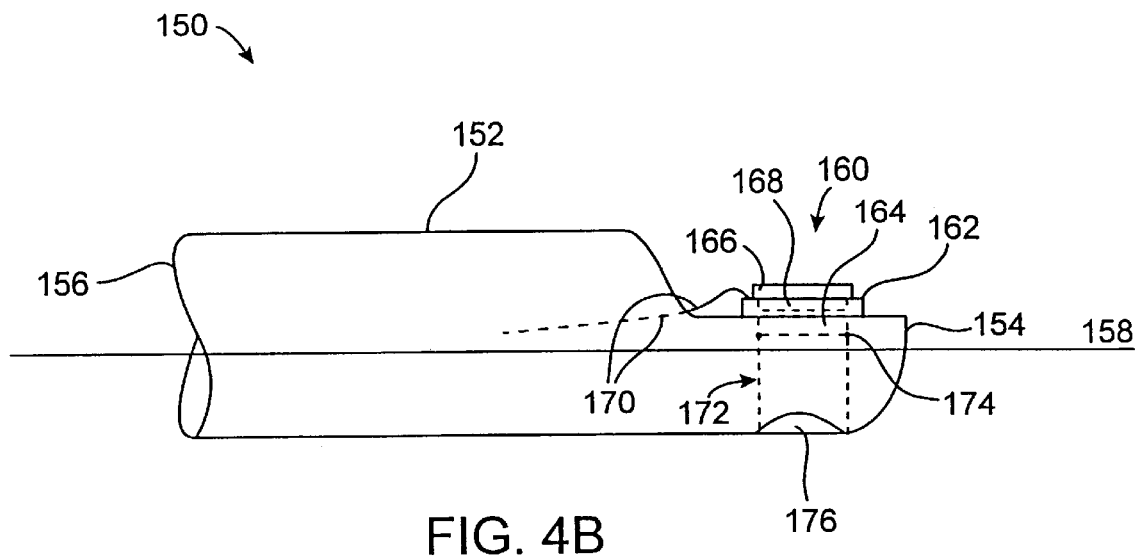
FIGS. 4A and 4B depict side views of alternative embodiments of an imaging assembly according to the present invention.
Figure 4A:
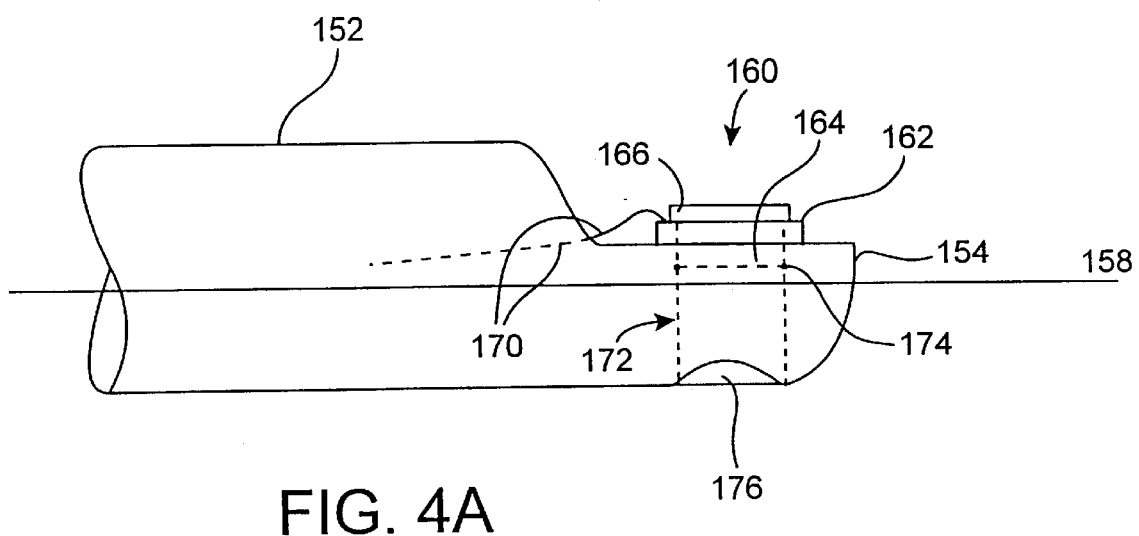

Turning now to FIGS. 4A and 4B, alternative imaging assemblies according to the present invention will be described. An imaging assembly 150 includes a housing 152, having a distal end 154, a proximal end 156 and a longitudinal axis 158. A transducer connection apparatus 160 is provided, having a washer 162, a transducer element 164 and a matching layer 166. FIG. 4B depicts apparatus 150 also having a bond layer 168 disposed within washer 162 hole. Connection apparatus 160 is similar to connection apparatus 10 described in conjunction with FIGS. 1 and 2.

Imaging assembly 150 includes a lead 170, and an air-filled cavity 172 in housing 152. Cavity 172 may comprise a throughhole as shown in FIG. 2 with a cap 176 enclosing a second end of the throughhole. Alternatively, cavity 172 may comprise a cavity that does not extend completely through housing 152. Since air has an acoustic impedance of about 0.0004 megarayls, air-filled cavity 172 provides a nearly perfect reflection. Therefore, ultrasound waves typically will not emanate from the cavity-facing side of transducer element 164. Imaging assembly 150 may have one or more matching layers 166. As shown in FIG. 4B, imaging assembly 150 has bond layer 168 acting as the second matching layer for transducer element 164. Since transducer element 164 cannot be operably attached to a backing material in assembly 150, transducer element 164 preferably is operably attached to the interior walls of cavity 172 using at least one attachment point 174. Attachment points 174 may comprise electrically conductive epoxy, or the like. Alternatively, a back side electrical connection or ground connection may be established by operably attaching transducer element 164 to washer 162, provided washer 162 is electrically conductive and is operably attached to housing 152.

Figure 5A:
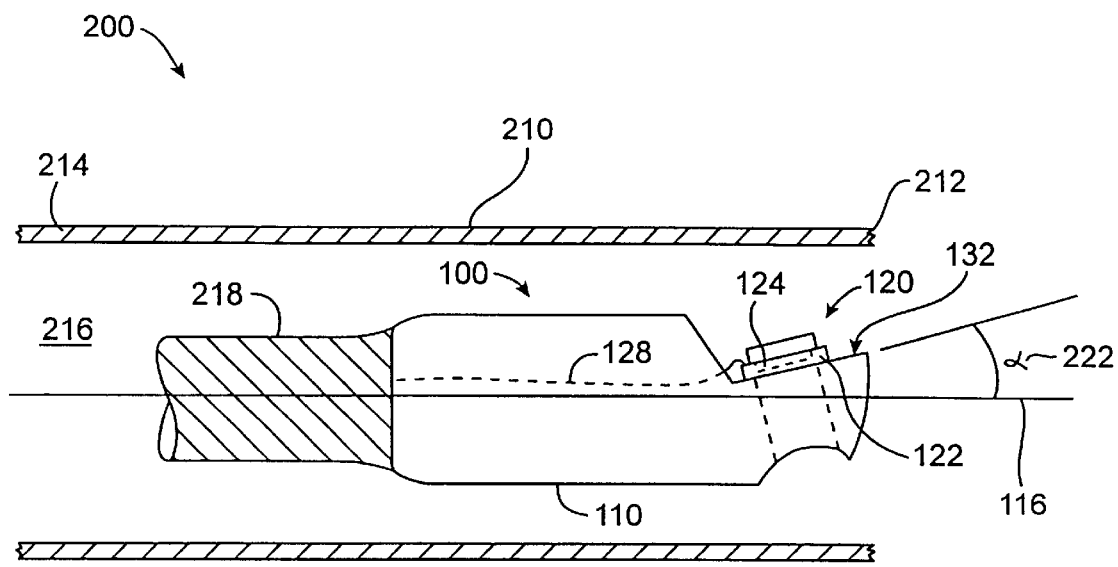
FIGS. 5A and 5B depict partial cross-sectional side views of catheter systems according to the present invention.
Figure 5B:
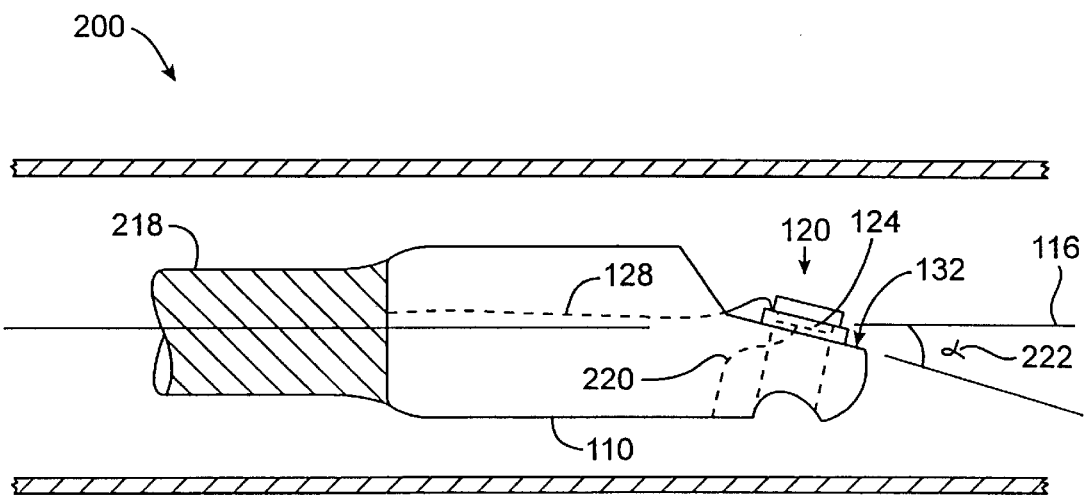

Turning now to FIGS. 5A and 5B, a catheter system 200 according to the present invention will be described. Catheter system 200 comprises a catheter body or sheath 210 having a distal end 212, a proximal end 214, and a working lumen 216. Sheath 210 preferably is fully sonolucent, or includes a portion of sonolucent material, to provide desirable acoustic transmissiveness. Sheath 210 may comprise nylon, polyethylene or the like. Imaging assembly 100 is disposed within lumen 216 and operably attached to a cable 218. Cable 218 preferably comprises an integrated coaxial/drive cable. Exemplary cables 218 are described in U.S. patent application Ser. No. 09/017,578, entitled "Integrated Coaxial Transmission Line and Flexible Drive Cable", the complete disclosure of which is hereby incorporated by reference. Imaging assembly 100 preferably is operably attached to a distal end of cable 218 by welding, electrically conductive adhesive or the like. This results in a mechanical connection between imaging assembly 100 and cable 218. Rotation of cable 218, in turn, rotates imaging assembly 100.

Imaging assembly 100, and in particular, connection apparatus 120, are essentially as described in conjunction with FIG. 3. As shown in FIGS. 5A and 5B, housing 110 is formed with surface 132 having a desired angle 222 with respect to axis 116. Angle 222 preferably is between about +60 degrees and about −60 degrees, and more preferably, between about +15 degrees (as approximately shown in FIG. 5A) and about −15 degrees (as approximately shown in FIG. 5B). By creating angle 222, ultrasound signals transmitted by transducer element 124 are less likely to be reflected by sheath or catheter body 210 during operation of catheter system 200.

By forming housing 100 so that surface 132 is at known angle 222 with respect to axis 116, transducer element 124 likewise is positioned at a known angle with respect to axis 116. In contrast, attaching transducer element 124 by hand to the inside of cavity 130, as may be done in the prior art, results in variations in the angle between axis 116 and transducer element 124. Therefore, catheter system 200 reduces or eliminates the catheter-to-catheter variation in angle 222 that typically occurs when transducer element 124 is attached by hand.

As shown in FIGS. 5A and 5B, lead 128 preferably is operably attached to washer 122 and to cable 218. In this manner, an electrical connection is established between transducer element 124 and cable 218. Cable 218, preferably an integrated coaxial/drive cable, then can be used to transmit signals from transducer element 124 to desired electronics, such as ultrasound imaging electronics maintained outside a patient's body. Similarly, the desired electronics can transmit a signal through cable 218, through lead 128, and to washer 122. As previously discussed, a positive electrical connection is made between washer 122 and transducer element 124 to allow the signal to reach transducer element 124. Lead 128 may comprise a center wire or lead from integrated coaxial/drive cable 218. In such an embodiment, the coaxial cable shield (not shown in FIG. 5) is terminated at a distal end of drive cable 218. The coaxial center wire or lead comprises, or operably attaches to, lead 128. Lead 128 is operably attached to washer 122, as previously discussed. A back side electrical connection or negative connection or ground is established between transducer element 124 and housing 110 as previously discussed. For example, a second electrode 220 may be used to connect a cavity-facing side of transducer element 124 to housing 110 or to the coaxial cable shield (not shown).

The operation of catheter system 200 comprises inserting catheter system 200 into a patient and positioning imaging assembly 100 at a desired location within the patient's anatomy. Drive cable 218 is rotated which, in turn, rotates imaging assembly 100 containing transducer element 124. Transducer element 124 is excited using an electrical or other signal transmitted through cable 218 and into transducer element 124. Transducer element 124 propagates ultrasound signals into the patient's tissue surrounding the imaging assembly 100. Ultrasound signals reflect off the patient's tissue and are received by transducer element 124. The present invention, using improved transducer connection apparatus, reduces or eliminates the signal interference typically caused by attaching a lead or electrode to the transducer element 124 surface. The reflected signals are transmitted through cable 218 to ultrasound signal processing electronics which produces an image of the patient's tissue.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A catheter system, comprising:
    a catheter body having a distal end, a proximal end and a working lumen;
    a cable disposed within said working lumen; and
    an imaging assembly operably attached to a distal end of said cable, said imaging assembly comprising
       a housing; and
       a transducer connection apparatus operably attached to said housing, said connection apparatus comprising
          a washer having a hole therethrough;
          a transducer element at least partially disposed within said washer hole; and
          a matching layer operably attached to said washer;
    wherein said transducer element is in electrical communication with said washer.

2. A catheter system as in claim 1, wherein said cable comprises an integrated coaxial/drive cable.

3. A method of imaging a body lumen comprising:
    providing a catheter system comprising,
       a catheter body having a distal end, a proximal end and a working lumen;
       a drive cable and a transmission line disposed within said working lumen;
       a housing having a distal end, a proximal end operably attached to said drive cable, a longitudinal axis and a transducer connection apparatus operably attached to said housing, said connection apparatus comprising,
          a washer having a hole therethrough;
          a transducer element at least partially disposed within said washer hole; and
          a matching layer operably attached to said washer and adapted to be in electrical communication with said transducer element such that an electrical connection is established between said washer and said transducer element;
    inserting said catheter into a body lumen;
    energizing said transducer element;
    capturing a reflected signal; and
    producing an image of said body lumen based on said reflected signal.

4. The catheter system as in claim 1 wherein said transducer element is in electrical communication with both said housing and said cable.

5. The catheter system as in claim 1 wherein said cable comprises a transmission line that is in electrical communication with said washer.

6. The catheter system as in claim 1 wherein at least a portion of said matching layer comprises an electrically conductive material.

7. The catheter system as in claim 1 wherein said matching layer is operably attached to said washer using an electrically conductive adhesive material.

8. The catheter system as in claim 1 wherein said washer comprises a flexible circuit.

9. The catheter system as in claim 1 wherein at least a portion of said washer comprises an electrically conductive material.

10. The catheter system as in claim 1 wherein said washer has an outer diameter/major axis and an inner diameter/major axis, said washer outer diameter/major axis being greater than a matching layer diameter/major axis.

11. The catheter system as in claim 10 wherein said matching layer diameter/major axis is greater than said inner diameter/major axis.

12. The catheter system as in claim 1 wherein said transducer element is fully disposed within said washer hole.

13. The catheter system as in claim 1 wherein a portion of said housing forms a generally flat surface to which said connection apparatus is operably attached, said surface positioned at a desired angle relative to said housing longitudinal axis, said desired angle between about −60 degrees and about +60 degrees.

14. The catheter system as in claim 1 wherein said housing is formed with a throughhole, and wherein said washer is operably attached to said surface to at least partially cover a first opening of said throughhole.

15. The catheter system as in claim 14 further comprising a backing material in said throughhole, said backing material comprising an electrically conductive material and wherein said transducer element is in electrical communication with said backing material.

16. The catheter system as in claim 14 wherein said housing further comprises a cap to enclose a second opening of said throughhole to create an air-filed cavity.

17. A catheter system, comprising:
    an elongate catheter body having a working lumen;
    a cable disposed within said working lumen; and
    an imaging assembly operably attached to a distal end of said cable, said imaging assembly comprising
       a housing; and
       a transducer connection apparatus operably attached to said housing, said connection apparatus comprising
          a washer having a hole therethrough;

a transducer element at least partially disposed within said washer hole; and a matching layer operably attached to said washer and to said transducer element.

18. The catheter system as in claim 17 wherein said transducer element is fully disposed within said washer hole.

19. The catheter system as in claim 17 wherein said matching layer is operably attached to said washer and said transducer element to establish an electrically conductive path between said transducer element and said washer.

20. The catheter system as in claim 19 wherein said cable further comprises a transmission line, said transmission line in electrical communication with said washer.

* * * * *